United States Patent [19]
Beysens et al.

[11] Patent Number: 6,141,088
[45] Date of Patent: Oct. 31, 2000

[54] METHOD AND DEVICE FOR CHARACTERIZING A MODIFICATION IN TIME OF THE STATE OF CONDENSATION OF DROPLETS ON A TARGET

[75] Inventors: Daniel Beysens, Egreve; Maria Marcos-Martin, Boulogne Billancourt, both of France; Vadim Nikolayev, Metairie, Ukraine; Patrick Sibille, Mons, France

[73] Assignee: Commissariat a l'Energie Atomique, Paris, France

[21] Appl. No.: 09/254,933

[22] PCT Filed: Sep. 15, 1997

[86] PCT No.: PCT/FR97/01623

§ 371 Date: Aug. 17, 1999

§ 102(e) Date: Aug. 17, 1999

[87] PCT Pub. No.: WO98/12546

PCT Pub. Date: Mar. 26, 1998

[30] Foreign Application Priority Data

Sep. 17, 1996 [FR] France ................................ 96 11310

[51] Int. Cl.⁷ .............................. G01B 11/00; G01N 21/00
[52] U.S. Cl. .............................. 356/72; 356/372; 356/379
[58] Field of Search .............................. 356/73, 372, 379, 356/380, 72

[56] References Cited

FOREIGN PATENT DOCUMENTS

| 0 409 546 | 1/1991 | European Pat. Off. . |
| 24 04 006 | 8/1975 | Germany . |
| 92 18854 | 10/1992 | WIPO . |

OTHER PUBLICATIONS

Langmuir, 1995 11, "From Droplet Growth to Film Growth on a Heterogeneous Surface Condensation Associated with a Wettability Gradient", Hong Zhao and Daniel Beysens.

*Optics Communications*, vol. 91, No. 1/02, 1 Juillet 1992, pp. 5–8, XPOOO278055, "Determination of the Dew Point Using Laser Light and a Rough Surface," Shigeaki Matsumoto et al.

*Sensors and Actuators A*, vol. A42, No. 1/03, 15 Avril 1994, pp. 503–507, XPOOO449970 "Hygrometer with Fibre Optic Dew Point Detector," Jachowicz R S et al.

*Bulletin du Bnm*, n 89, Juillet, 1992, "Exploitation Statistique Des Resultats D'Etalonnage Des Hygrometres a Condensation a Detection Optique," B. Cretinon and L. Morin.

*Agricultural and Forest Meteorology*, 62 (1992) 263–274, "Estimating Dew Duration on Banana and Plantain Leaves from Standard Meteorological Observations," Jean–Paul Lhomme and Francisco Jimenez O.

*Primary Examiner*—F. L. Evans
*Attorney, Agent, or Firm*—Burns Doane Swecker & Mathis L.L.P.

[57] ABSTRACT

An apparatus and method for characterizing a modification of the state of condensation of liquid droplets on a target (10). The apparatus comprises a light transmitting means (20, 21) capable of directing a light beam (42) towards the target (10), a photodetector (48) capable of measuring the intensity of a beam (46) reflected/ transmitted from the target and of transmitting a measuring signal, a unit (50) for processing the measuring signal connected to the photodetector and capable of recording a function a(t) defined by $$a(t) = \frac{I(t)}{I_i};$$

where $I_i$ is the intensity of the reflected/ transmitted beam measured without droplets being on the target, and capable of determining, from function a(t), a characteristic of the state of condensation of the droplets. Application in biological decontamination and meteorology.

17 Claims, 4 Drawing Sheets

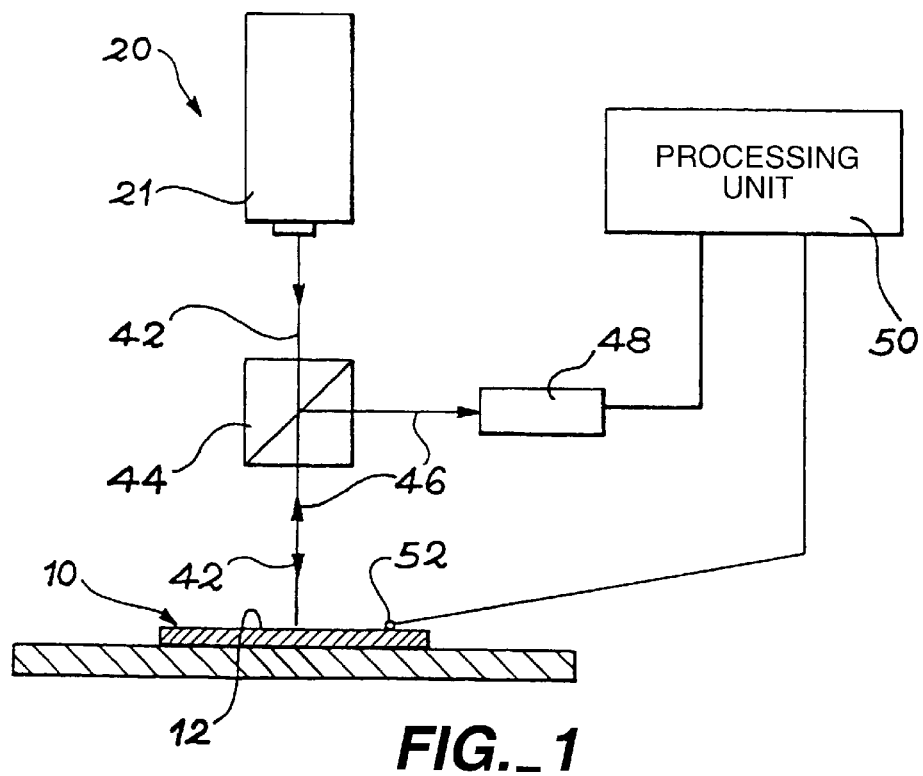
FIG._1
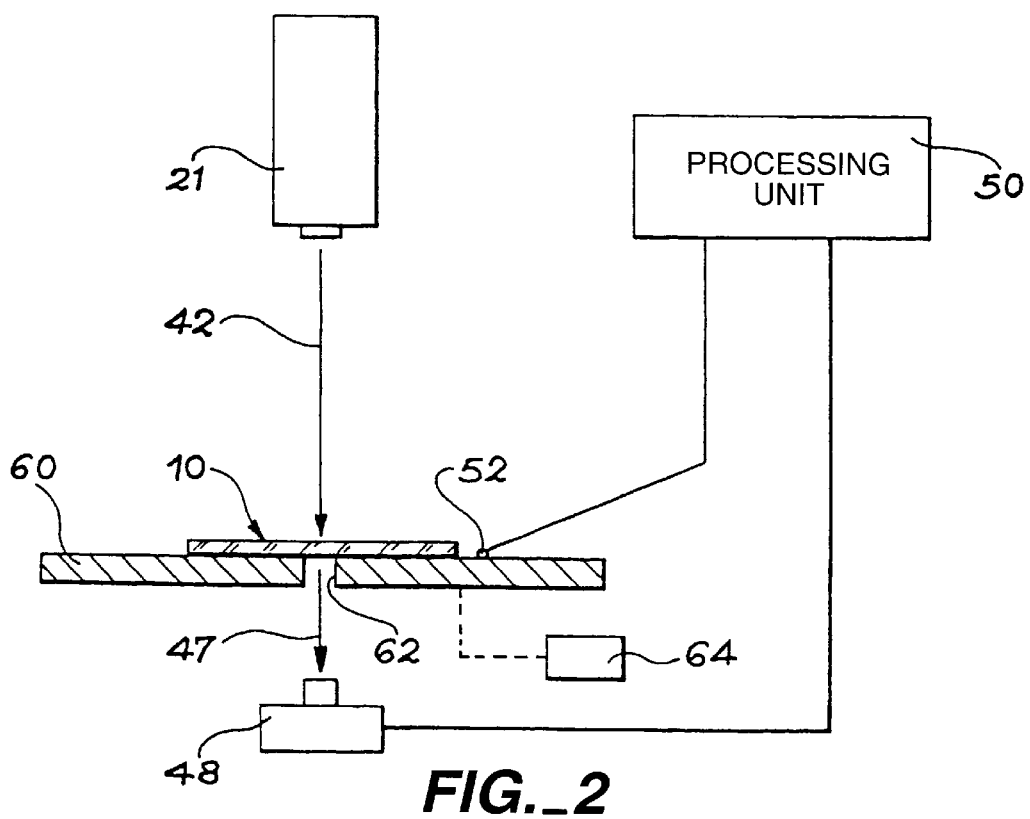
FIG._2

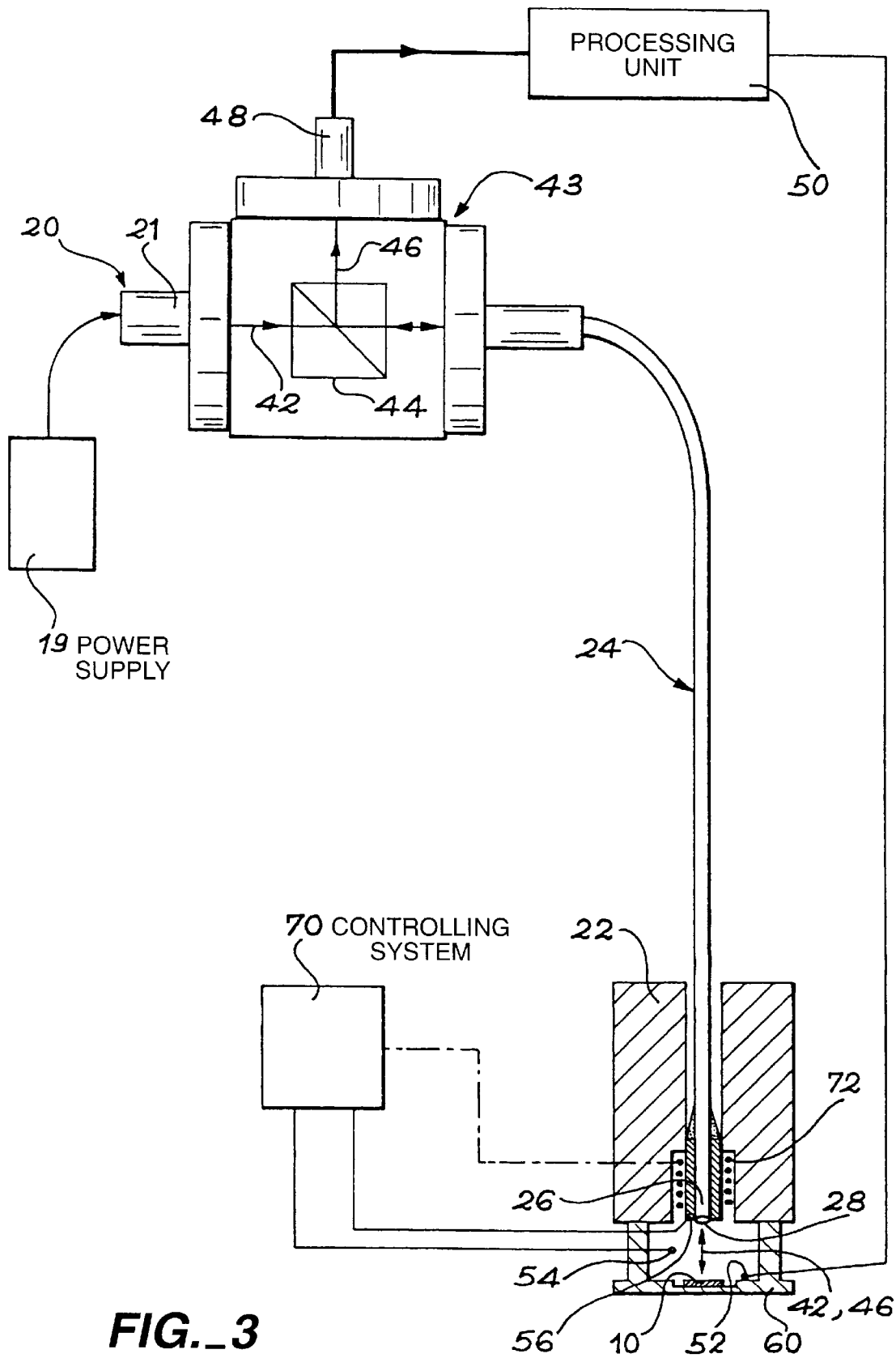
FIG._3

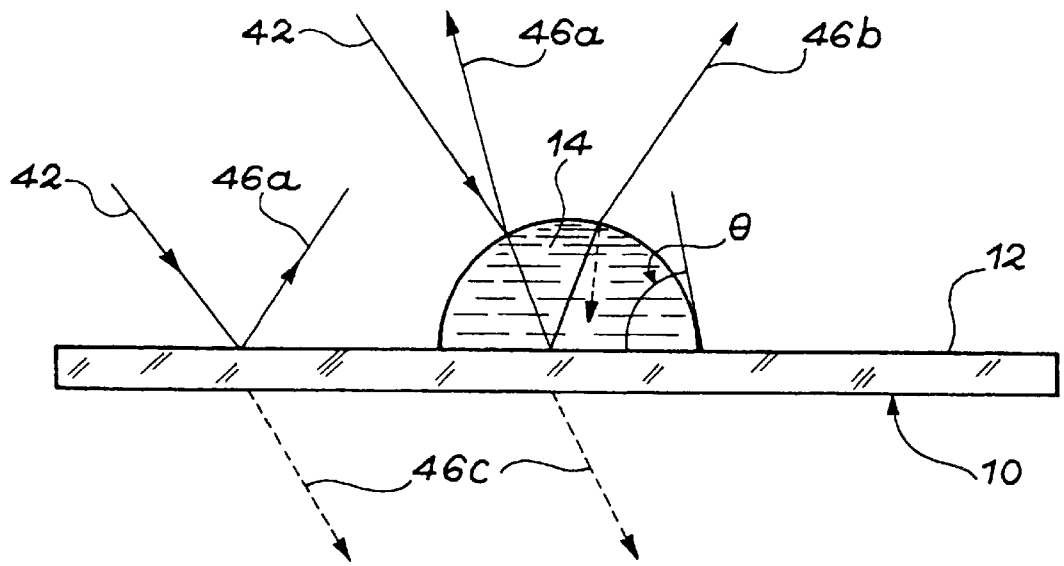
FIG._4
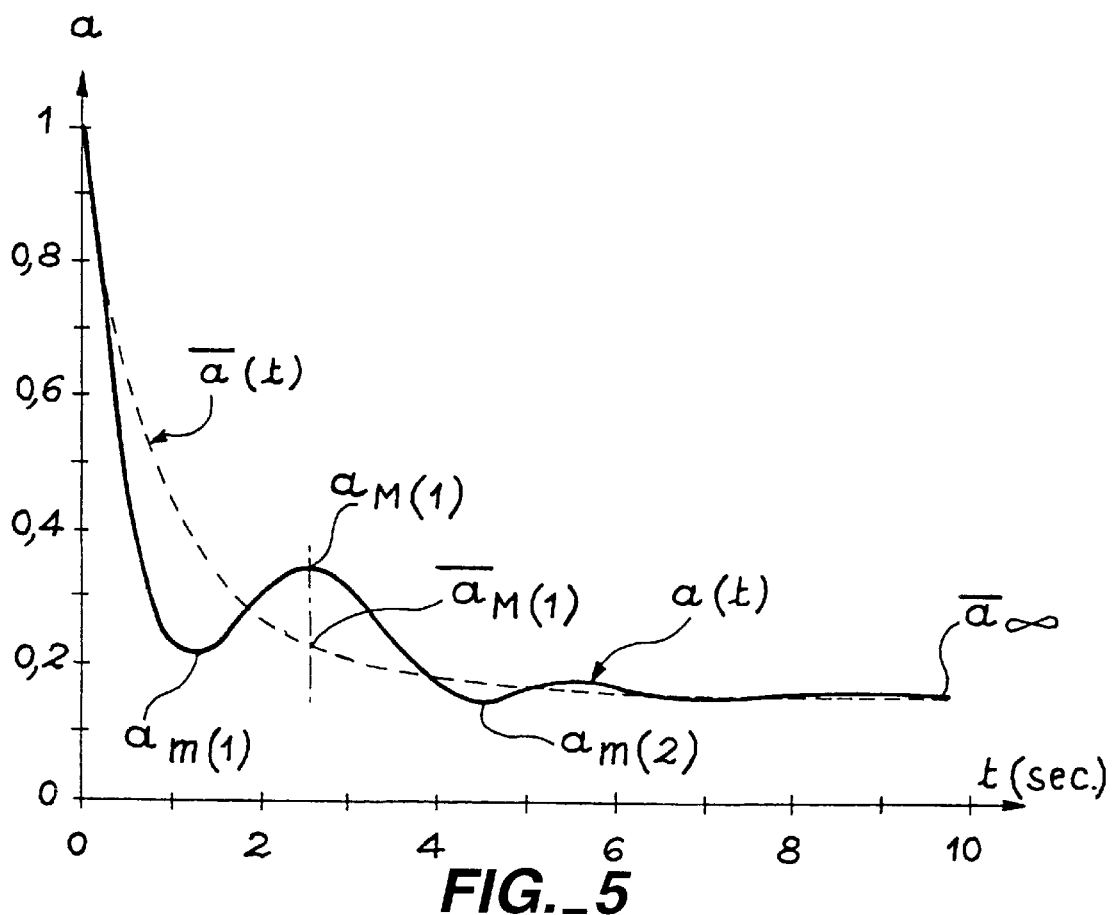
FIG._5

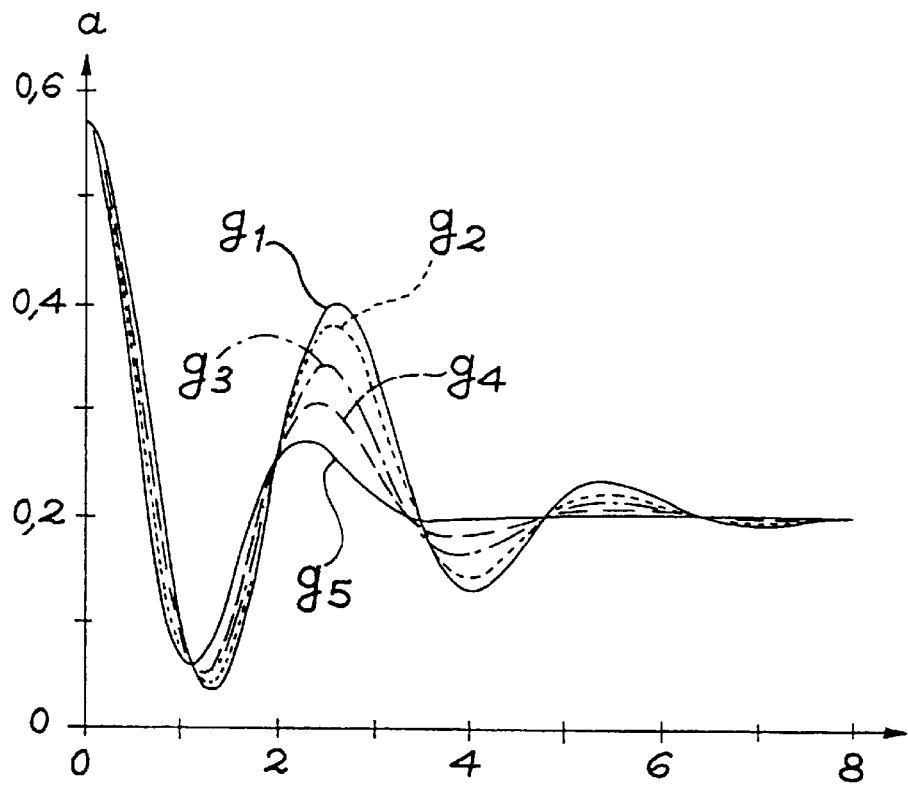
FIG._6
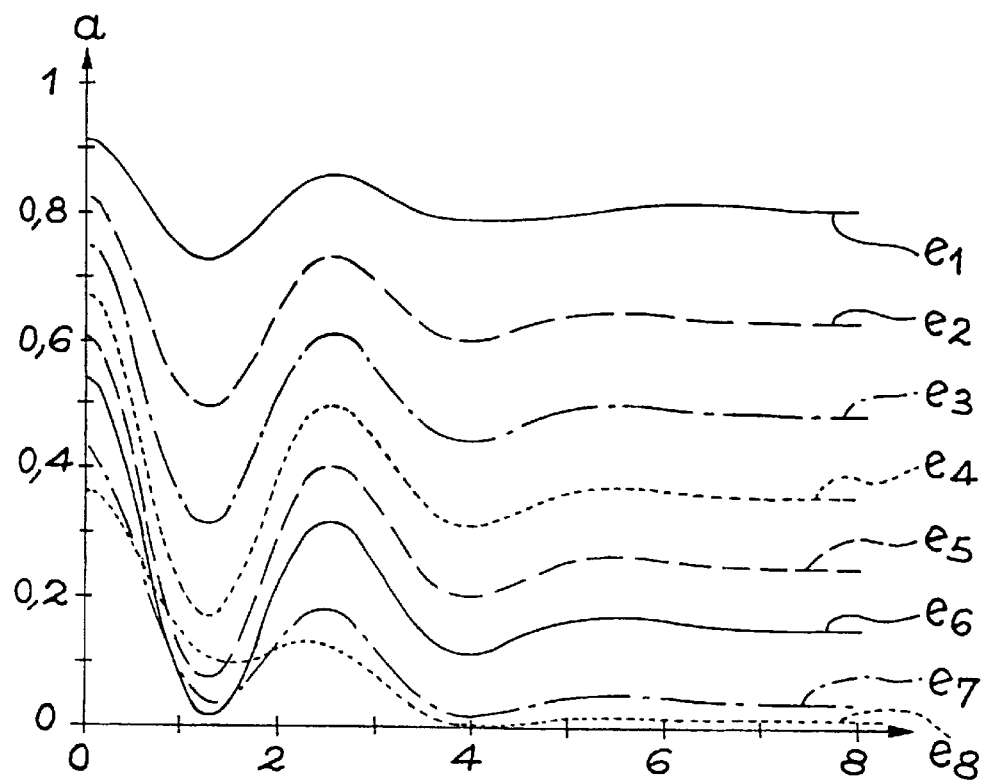
FIG._7

METHOD AND DEVICE FOR CHARACTERIZING A MODIFICATION IN TIME OF THE STATE OF CONDENSATION OF DROPLETS ON A TARGET

TECHNICAL FIELD

This invention relates to a method and apparatus for characterizing a modification in time of the state of condensation of liquid droplets on a target.

The method and apparatus of the invention namely allow for measuring the condensation or evaporation of droplets on the target. They also allow for measuring the parameters ruling the condensation of the droplets.

The fields of application of the invention are widely varied. By way of example, the invention can be used advantageously in the biological field for checking the state of sterilization of a surface by measuring the condensation of a germicide. In fact, it allows for determining whether the germicide is present on a surface for a sufficient time and in sufficient quantity for sterilizing it.

The invention can also be used in the field of meteorology, e.g. for measuring the characteristics of dew. It may also serve for determining the appropriateness of a preventive treatment of certain plants subject to cryptogamic diseases due to the presence of dew.

Furthermore, the invention can be used advantageously for measuring the condensation of water in dune sand.

STATE OF THE ART

For characterizing the state of condensation of liquid droplets on a target, at present, essentially two parameters are being used, which are the measure of the dew temperature and the measure of the condensed liquid mass.

In fact, a number of optical sensors, capable of determining the dew temperature for a target, and consequently the ambient vapor tension, are known. On this subject, we refer to document (1), the reference of which is mentioned at the end of this specification.

The principle for determining the dew temperature for a given substance is based on the measure of the reflection or transmission of a light beam by a plane target substrate whose temperature is lowered. When the substrate has reached the so-called dew temperature, condensation of the substance's droplets on the target occurs. The reflection or transmission of the light beam is then almost nil.

However, it can be noticed that the measured temperature at which the condensation phenomenon (dew) occurs always exceeds the dew temperature corresponding to a homogeneous condensation. This discrepancy is due to the fact that the contact angle of the condensation droplets on the target surface never equals 180°.

Also, apparatuses for measuring the dew temperature are known, wherein the target is designed so that the reflection of a light beam thereon is almost nil in the absence of droplet condensation.

The dew temperature is then determined by lowering the target's temperature and measuring it when the reflection of the light beam goes from zero to a non zero value due to the formation of a film of condensed liquid.

On this subject, we refer to document (2), the reference of which is mentioned at the end of the specification.

The second known method for determining the state of condensation consists in measuring the mass of the condensed liquid. This method, as described in document (3), the reference of which is mentioned at the end of the specification, is widely used in agricultural meteorology. In accordance with this method, a substrate, as condensation target, is weighed before, during and after condensation.

According to a variant, it is also known to sample part of the condensed liquid with a paper towel and to weigh this towel.

The techniques set forth above are not easy to implement and only provide little information on the condensation building up on the target.

In fact, as shown in document (4), the reference of which is mentioned at the end of this specification, the droplets formed through condensation may be characterized by other magnitudes and namely by their contact angle to the target surface.

SUMMARY OF THE INVENTION

It is an objective of the invention to provide a method and apparatus for determining the state of condensation of a liquid on a target, without the restrictions of the methods previously described, and allowing to establish, if required, a large number of parameters characterizing the state of condensation.

In addition, it is an objective of the invention to provide an apparatus making it possible to simulate the condensation on an artificial target for measuring thereon the characteristics of the state of condensation.

To achieve these objectives, the object of the invention is more specifically a method for characterizing a modification in time of the state of condensation of liquid droplets on a target. This modification may concern both condensation and evaporation. In accordance with the method of the invention, a light beam is directed towards the target, an intensity I(t) of a beam transmitted through the target or a beam reflected from the target is measured in time (t), and a time function a(t) is recorded which is defined by $$a(t) = \frac{I(t)}{I_i}$$

where $I_i$ is an intensity of the transmitted or reflected beam, measured without droplets being on the target, and from function a(t), and more precisely from its time form, at least one characteristic of the state of condensation is determined.

According to a particular aspect of the invention, it is possible to determine a characteristic of the state of condensation from at least one datum chosen from:

- a time value (t) of function a(t),
- a smoothing value at time (t) of function a(t), labeled as $\bar{a}(t)$,
- an asymptotic value of function a(t), labeled as $\bar{a}\infty$,
- the value of a first local maximum of function a(t) labeled as $a_M(1)$,
- a smoothing value of function a(t) at a time (t) corresponding to the first local maximum of function a(t), and labeled as $\bar{a}_M(1)$.

As understood by the invention, the smoothing value of function a(t) is meant to designate the value at the time t of a monotone function $\bar{a}(t)$ as close as possible to function a(t).

According to a particular implementation of the inventive method, the characteristic of the state of condensation established can be the presence or absence of droplets, respectively. This characteristic is determined by the following criteria:

a(t)=1 for absence of droplets and a(t)<1 for presence of droplets.

In fact, when a(t)=1 at a given instant t, it is verified that $I(t)=I_i$, i.e. that the target is in a state where its surface has no condensation droplets.

Once droplets have appeared, the transmitted or reflected light beam is weakened due to a dispersion of light passing through the droplets. It is then verified that $I(t)<I_i$ and consequently a(t)<1.

According to a particular aspect of the invention, it is possible to determine a geometric characteristic of the state of condensation. The geometric characteristic is meant to designate any characteristic related to the shape and size of the droplets, as well as to their arrangement on the target.

Among the geometric characteristics, the proportion of the surface filled by the droplets on the target, the contact angle of the droplets, their polydispersivity, their radius, their volume, etc., can be mentioned.

By way of example, the characteristic of the state of condensation established can be the proportion at the time t of the surface filled by the droplets, said surface proportion, labeled as $\epsilon^2(t)$, being defined by the formula:

$$\varepsilon^2(t) = 1 - \sqrt{\overline{a(t)}}$$

According to another example, the average radius <R> of the droplets can be determined for at least one of the first local minimum, the second local minimum and the first local maximum of function a(t), <R> being defined by

* <R>=λF at a first minimum of function a(t)
* <R>=2λF at the first maximum of function a(t)
* <R>=3λF at a second minimum of function a(t)

where λ is the wavelength of the incident light beam, and where F is defined by $$F = 15\exp\left(-\frac{\theta}{45}\right).$$

The value θ is understood as the average contact angle (in degrees) of the droplets on the target.

Considering a geometric factor f(θ) linking the volume of a droplet together with its radius, it is also possible to compute at the time (t) the volume v(t) of the condensed liquid per unit area of the target.

This volume v(t) is given by the following formula:

$$v(t) = \frac{f(\theta)\langle R\rangle}{\pi}\varepsilon^2(t).$$

According to a particular implementation of the inventive method, the angle θ, expressed in degrees, can be established in accordance with the following formula:

$$\theta = 200\cdot\sqrt{\overline{a}^\infty}$$

According to another particular implementation of the invention, the characteristic of the state of condensation established is the polydispersivity of the droplets, labeled as g and defined by:

$$g = 1.25\cdot\left(0.3 - \frac{\delta}{5}\right)$$

and where $$\delta = \frac{a_M(1) - \overline{a}_M(1)}{\overline{a}_M(1)}$$

The values $a_M(1)$ and $\overline{a}_M(1)$ are respectively the values of the curves a(t) and $\overline{a}(t)$ at the instant of the first local maximum of curve a(t).

As understood by the present invention, the polydispersivity of the droplets designates the distribution of their radius around the average radius.

Polydispersivity is defined by $$g = \sum \frac{(R^2 - \langle R\rangle^2)^{1/2}}{\langle R\rangle}$$

where R is the radius of an individual droplet, <R> the average radius of the droplets, defined by $$\langle R\rangle = \frac{\sum R^2}{\sum R}$$

and Σ a sum sign symbolizing the sum of all target droplets.

An apparatus for characterizing a modification of the state of condensation of liquid droplets on a target is also an object of the present invention. This apparatus comprises:

a light transmitting means capable of directing a monochromatic light beam towards the target, a photodetector capable of measuring the intensity of a beam reflected from the target or a beam transmitted through the target, and of transmitting a measuring signal, a measuring signal processing unit connected to the photodetector and capable of recording a time function a(t) defined by $$a(t) = \frac{I(t)}{I_i}$$

where $I_i$ is the intensity of the reflected or transmitted beam, respectively, measured without droplets being on the target. The processing unit is furthermore capable of determining, from function a(t), at least one characteristic of the state of condensation of the droplets.

According to a particular aspect of the invention, the apparatus can also comprise a heat sensor for measuring the target temperature. The heat sensor is connected to the computing unit for determining A dew point when the droplets are condensing on the target.

Due to this aspect of the invention, the dew temperature can be determined additionally in a manner that is known and described in the introductory part of the specification.

According to a special embodiment of the inventive apparatus, the light transmitting means can comprise:

a monochromatic light source, a detector head for collimating the incident light beam on the target and receiving the reflected beam, a fiber optic link connecting the detector head to the light source and the photodetector.

According to a development of the invention, the detector head can be fitted with a temperature controlling means. This means comprises e.g. a thermocouple capable of measuring the temperature of the detector head and a heating resistor controlled according to the temperature of the head and that of the target, so as to maintain the temperature of the detector head at a value slightly higher than that of the target. Thus, condensation of the liquid droplets on the detector head is avoided.

Further characteristics and advantages of the invention will be more apparent from the following description with reference to the drawings of the accompanying figures, provided for illustration purposes only and not to be restrictive.

BRIEF DESCRIPTION OF THE FIGURES

FIG. 1 is a concept diagram of an apparatus in accordance with the invention operating in reflection mode.

FIG. 2 is a concept diagram of a n apparat us in accordance with the invention operating in transmission mode.

FIG. 3 is a diagram corresponding to a particular embodiment of the inventive apparatus operating in reflection mode.

FIG. 4 is a larger scale diagram of a detectora's measuring target in accordance with the invention.

FIG. 5 is a chart showing the function curves a(t) and $\bar{a}(t)$ in time, representative of the state of condensation of droplets on the target.

FIG. 6 is a nomogram linking the value a of function a(t) together with the radius of the droplets formed during condensation, and for different values of the droplets' polydispersivity.

FIG. 7 is a nomogram linking the value a of function a(t) together with the average radius of the droplets for different values of the surface fraction of the target filled by the droplets.

DETAILED DESCRIPTION OF THE EMBODIMENTS OF THE INVENTION

FIG. 1 shows the main components of an apparatus in accordance with the invention for determining the state of condensation of a liquid on a target 10.

Target 10 has an upper reflecting surface 12 whereon the characteristics of the liquid's condensation droplets are to be measured and determined.

Advantageously, when measures are to be carried out on a medium with a non-light reflecting surface this medium can be replaced by a reflecting target having a wetting characteristic identical to that of the medium.

The apparatus of FIG. 1, suitable for carrying out measures on a reflecting target comprises light transmitting means 20. This means is fitted, e.g. with a He-Ne type laser 21 with a 1 to 5 mW output and a 0.6328 μm wavelength λ, capable of transmitting a monochromatic light beam 42 directed perpendicularly towards target 10.

The beam 42, also called incident beam, passes through a semitransparent reflecting cube 44 before reaching the target. Cube 44 is transparent for beam 42, which it lets pass through. On the other hand, it is designed for deflecting a beam 46 reflected by the target, towards a photodetector 48.

Due to the normal incidence of the incident beam 42 on the target in the case of the figure described, this beam is substantially merged with the reflected beam on the section of the optical path comprised between reflecting cube 44 and target 12.

Photodetector 48 comprises, e.g. a photodiode capable of transmitting an electric measuring signal depending on the intensity of the reflected beam that reaches it. The photodetector is connected to a unit 50 for processing the electric measuring signal. Unit 50 is for instance a microcomputer running under some programmed software.

As specified before, processing unit 50 is capable of recording a function a(t) defined by $$a(t) = \frac{I(t)}{I_i}$$

where I(t) and $I_i$ are respectively the intensity of the beam reaching the photodetector at the time (t) and the intensity of the beam reaching the photodetector when there are no droplets on the target.

The processing unit also allows to calculate, from function a(t), the characteristic magnitudes of the state of condensation according to the previously specified formulae.

A heat sensor, in the form of a thermocouple 52, is installed on the target and is connected to the signal processing unit. Due to the heat sensor, it is possible in a conventional way to determine also the dew temperature, i.e. the temperature from which on condensation occurs. The start of the condensation is made out by detecting a modification of the reflected beam intensity.

FIG. 2 shows in a diagram a variant of the apparatus of FIG. 1, suitable for carrying out transmission measures on a substantially transparent target.

Parts of FIG. 2 identical or similar to those of FIG. 1 have the same reference numerals. Thus, reference can be made to the preceding description. In the apparatus of FIG. 2, the laser 21, forming a light source, directly sends an incident beam 42 of monochromatic light towards target 10.

Target 10 lies on a medium 60 that has an opening 62 through which passes the beam transmitted through target 10. This beam is identified by reference numeral 47. Beam 47 is intercepted by a photodetector 48 that measures its intensity.

Photodetector 48, as well as a heat sensor 52, is linked to signal processing unit 50. It can be noticed that sensor 52 is not directly fixed on the target, but on the medium 60 that is in thermal contact with target 10 and substantially at the same temperature as the latter.

According to a particular aspect, illustrated in a rough diagram in FIG. 2, a target temperature controlling means 64 can be provided. This is, e.g. a Peltier effect type cooling block in thermal contact with medium 62.

It can be noticed that a similar controlling means can also be provided for the apparatus operating with a reflecting target, as represented in FIG. 1.

FIG. 3 shows a particular embodiment of the apparatus of FIG. 1.

In the embodiment of FIG. 3, the light transmitting means comprises different sections arranged on either side of an optical splitter 43. The optical splitter is fitted with a semitransparent reflecting cube 44.

The light transmitting means comprises a laser diode 21 connected to an electric power supply 19 arranged on the first side of splitter 43 and capable of transmitting incident beam 42. Light transmitting means 20 also comprises a detector head 22 connected to a second side of optical splitter 43, opposite the first side, via an optical fiber 24. Cube 44 is designed to let through the incident beam from the laser diode to the optical fiber and deflect a beam from the detector head.

One end 26 of the optical fiber opens onto the inside of detector head 22 on a focussing lens 28 allowing to send a collimated incident beam 42 onto target 10. Target 10 is arranged on a detector head medium 60, especially provided for this purpose.

Lens 28 also allows for collecting a beam reflected by target 10 for directing it into the optical fiber. Thus, the optical fiber allows to transmit, without any loss, the incident light beam and the reflected light beam 46 between lens 28 and the optical splitter.

It can be noticed that in splitter 43, the reflected beam 46 is deflected, by cube 44, towards a photodetector 48 arranged on a third side of splitter 43.

The apparatus of FIG. 3 also comprises several thermocouple heat sensors. As in the previous figures, a first sensor 52 is provided for measuring the temperature of target 10. This sensor 52, just like photodetector 48, is connected to signal processing unit 50.

Two other heat sensors 54, 56 are respectively provided for measuring the temperature (Tr) of the atmosphere at a short distance from the target and the temperature (Tf) at the end 26 of the optical fiber. Temperature (Tr) is measured, e.g. at 5 mm from the target.

Heat sensors 54 and 56 are electrically connected to a temperature controlling system 70. With the temperature controlling system 70 it is possible to control the supply of electric current to a heating wire 72 surrounding the optical fiber end 26.

The power supply of the heating wire is controlled so that the ambient temperature (Tr) and the fiber optical end temperature (Tf) are substantially the same.

Temperatures Tr and Tf can also be recorded, e.g. by the signal processing unit 50, for measuring the dew point temperature and the saturation pressure around the target.

FIG. 4 shows a target 10 at a much larger scale. The surface 12 of target 10 is represented with a droplet 14 of condensed liquid. Target 10 is preferably a mirror in the form of a oxidized, silane covered single crystal silicon film. According to the finish of surface 12, the droplet's contact angle θ may vary from about 10° to 100°. This angle is adjusted so as to simulate a given medium with a given wettability.

The figure shows an incident beam 42 reaching the target in an area without droplets and a beam 42 reaching droplet 14. The reflected beams are respectively represented with reference numerals 46a and 46b. As an indication, the figure also shows the beams 46c that would be transmitted if the target were transparent.

In the case of FIG. 4, the angle of incidence of the incident beam is represented as being different from 90° for better highlighting the reflected rays. However, in the method and the apparatuses of the invention, the angle of incidence is adjusted preferably, but not necessarily, at 90°. In this case, the incident beam and the reflected beams are geometrically merged.

The chart of FIG. 5 specifies as the ordinate the normalized value a of function a(t) and of the smoothed function a(t), labeled as $\bar{a}$(t). Time is specified as the abscissa and counted in seconds.

In the chart, it appears that the curve a(t) has a first local minimum, a first local maximum and a second local minimum for which the values of function a(t) are respectively $a_m(1)$, $a_M(1)$ and $a_m(2)$. The curve shows other local extremes more difficult to detect. The asymptotic value of functions a(t) and $\bar{a}$(t) is labeled $\bar{a}\infty$.

The values am, $\bar{a}\infty$, $a_m(1)$ and $a_M(1)$ are namely used for calculating the value of the contact angle, the average radius and the polydispersivity of the droplets. The calculation formulae previously specified are not repeated here. The characteristics of the state of condensation can be established not only by computation but also from lookup tables or else be plotted as represented in FIG. 6 and 7.

FIG. 6 is a nomogram linking the value a of function a(t) together with the average droplet radius for different values of polydispersivity g. In FIG. 6, several curves, referenced g1, g2, g3, g4, and g5, respectively correspond to a polydispersivity equal to 0.14; 0.16; 0.20; 0.24 and 0.30.

The value of a is given on the ordinate while the average droplet radius is specified on the abscissa. The average radius is specified in wavelength units.

FIG. 6 corresponds to a droplet condensation at an average contact angle of θ=104° for a proportion of the target surface filled by the droplets 68 $^2$, such as $\epsilon^2$=0.55.

FIG. 7 is a nomogram linking the value a of function a(t) together with the average droplet radius for different values of the proportion $\epsilon^2$ of the target surface filled by the droplets.

As for FIG. 6, the values of a are specified on the ordinate and the droplet radius, in wavelength units, is specified on the abscissa.

FIG. 7 corresponds to a droplet condensation at an average contact angle θ=104° and polydispersivity g=0.18. In this figure, several curves referenced e1, e2, . . . e8, respectively correspond to values of the proportion $\epsilon^2$ of the surface filled by the droplets, equal to 0.1; 0.2; 0.3; 0.4; 0.5; 0.6; 0.8 and 0.9.

Documents Quoted (1) B. Cretinon, L. Morin and Y. P. YU, "Exploitation statistique des résultats d'étalonnage des hygromètres á condensation á détection". Bulletin du BNM, 89 14 (1992); R. F. Pragnell, "The modern condensation dew point hygrometer". Measurement+control 22, 74 (1989).

(2) S. Matsumoto and S. Toyooka, "Determination of the dew point using laser light and a rough surface". Opt. Comm. 91, 5 (1992).

(3) J. P. L'Homme and O. F. Kimenez, "Estimation of the dew duration on banana and plantain leaves from standard meteorological observations", Agric. Forest. Meteorol. 62, 263 (1992).

(4) H. Zhao and B. Beysens, "From droplet growth to film growth on a heterogeneous surface: condensation associated with a wettability gradient". Langmuir 11, 627 (1995).

What is claimed is:

1. A method for characterizing a modification in time of the state of condensation of liquid droplets on a target (10), characterized by directing a light beam (42) towards the target (10), measuring in time (t) an intensity I (t) of a beam (47) transmitted through the target or a beam (46) reflected from the target, and recording a time function a (t) defined by $$a(t) = \frac{I(t)}{I_i}$$

where $I_i$ is an intensity of the transmission or reflection beam measured without droplets being on the target, and analyzing a time form of function a (t) for determining at least one geometric characteristic of the state of condensation.

2. The method according to claim 1, characterized in that a characteristic of the state of condensation is determined from at least one datum chosen from:

a time value (t) of function a (t), a smoothing value at time (t) of function a (t), labeled as $\bar{a}$(t), an asymptotic value of function a (t), labeled as $\bar{a}\infty$, the value of a first local maximum of function a (t) labeled as $a_M(1)$, a smoothing value of function a (t) at a time (t) corresponding to the first local maximum of function a (t), and labeled as $\bar{a}_M(1)$.

3. The method according to claim 2, characterized in that lighting is achieved in coherent light and in that characteristic of the state condensation is a proportion at time (t) of the surface filled by the droplets, said surface proportion, labeled as $\epsilon^2(t)$, being defined by the formula:

$$\epsilon^2(t) = 1 - \sqrt{\bar{a}(t)}.$$

4. The method according to claim 2, characterized in that the characteristic of the state of condensation is an average contact angle of the droplets, labeled as θ and defined by the formula:

$$\Theta = 200 \cdot \sqrt{\bar{a}\infty}$$

where θ is expressed in degrees.

5. The method according to claim 2, characterized in that the characteristic of the state of condensation is a polydispersivity of the droplets, labeled as g and defined by:

$$g = 1.25 \cdot \left(0.3 - \frac{\delta}{5}\right)$$

and where $$\delta = \frac{a_M(1) - \bar{a}_M(1)}{\bar{a}_M(1)}.$$

6. The method according to claim 2, characterized in that the characteristic of the state of condensation is the average droplet radius, labeled as <R> and determined for at least one of the first local minimum, the second local minimum and the first local maximum of function a (t), <R> being defined by

* <R>=λF at a first minimum of function a (t)
* <R>=2λF at the first maximum of function a (t)
* <R>=3λF at a second minimum of function a (t)

where λ is the wavelength of the incident light beam, and where F is defined by $$F = 15\exp\left(-\frac{\Theta}{45}\right)$$

and where $$\Theta = 200 \cdot \sqrt{\bar{a}\infty}.$$

7. The method according to claim 1, comprising a determination, at time t, of the condensed liquid volume v(t) per unit area of the target.

8. The method according to claim 7, volume v(t) being given by $$v(t) = \frac{f(\Theta)\langle R\rangle}{\pi}\epsilon^2(t)$$

where f (θ) is a geometric factor linking the volume of a droplet together with its radius.

9. The method according to claim 1, characterized in that the characteristic of the state of condensation is the presence, or absence, of droplets, this characteristic being determined by the following criteria:

a(t)=1 for absence of droplets and a(t)<1 for presence of droplets.

10. An apparatus for characterizing a modification of the state of condensation of liquid droplets on a target, characterized in that it comprises:

a light transmitting means (20,21,22,43) capable of directing a monochromatic light beam (42) towards the target, a photodetector (48) capable of measuring the intensity of a beam (46) reflected from the target or a beam (47) transmitted through the target, and of transmitting a measuring signal, a measuring signal processing unit (50) connected to the photodetector and capable of recording a time function a (t) defined by $$a(t) = \frac{I(t)}{I_i}$$

where $I_i$ is the intensity of the reflected or transmitted beam, measured without droplets being on the target, the processing unit being furthermore capable of analyzing a time form of function a (t) for determining from function a (t) at least one geometric characteristic of the state of condensation of the droplets.

11. The apparatus according to claim 10, characterized in that the processing unit (50) is capable of computing the characteristic of the state of condensation of the droplets from at least one datum chosen from:

a time value (t) of function a (t), a smoothing value at time (t) of function a (t), labeled as $\bar{a}(t)$, an asymptotic value of function a (t), labeled as $\bar{a}\infty$, the value of a first local maximum of function a (t) labeled as $a_m(1)$, a smoothing value of function a (t) at a time (t) corresponding to the first local maximum of function a (t), and labeled as $\bar{a}_M(1)$.

12. The apparatus according to claim 10, characterized in that it comprises a heat sensor (52) for measuring the target's temperature, the heat sensor being connected to the computing unit (50) for determining a dew point while the droplets are condensing on the target.

13. The apparatus according to claim 10, characterized in that the light transmitting means comprises:

a monochromatic light source (21), a detector head (22) for collimating the incident light beam on the target (10) and receiving the reflected beam, a fiber optic link (24) connecting the detector head (22) to light source (21) and photodetector (48).

14. The apparatus according to claim 13, characterized in that the detector head comprises a means (54, 56, 70, 72) for controlling its temperature.

15. The apparatus according to claim 10, characterized in that the light transmitting means is capable of directing the coherent light beam towards the target (10) according to a substantially normal incidence.

16. The apparatus according to claim 13, characterized in that it further comprises a semitransparent reflector (44) arranged between the monochromatic light source (21) and target (10), the semitransparent reflector being designed for letting the incident beam (42) through to the target and deflecting a beam (46) reflected by the target towards the photodetector.

17. An apparatus according to claim 10, characterized in that it further comprises a means (64) for controlling the target's temperature.

* * * * *